United States Patent [19]

Tranner

[11] Patent Number: 5,030,374

[45] Date of Patent: Jul. 9, 1991

[54] CLEAR NEUTRAL NON-FOAMING RAPIDLY-RINSABLE GEL FACIAL CLEANSER FORMULATION

[75] Inventor: Frank Tranner, Trumbull, Conn.

[73] Assignee: International Research and Development Corporation, Mattawan, Mich.

[21] Appl. No.: 380,863

[22] Filed: Jul. 17, 1989

[51] Int. Cl.⁵ .................. C11D 17/00; C11D 3/48; A61K 31/79
[52] U.S. Cl. ......................... 252/90; 252/106; 252/174.21; 252/174.22; 252/174.23; 252/174.24; 252/DIG. 2; 252/DIG. 5; 252/DIG. 14; 424/63; 424/81; 514/846; 514/847
[58] Field of Search ............ 252/90, 106, 174.21, 252/174.22, 174.23, 174.24, DIG. 2, DIG. 5, DIG. 14; 424/63, 81; 514/846, 847

[56] References Cited

U.S. PATENT DOCUMENTS

| | | | |
|---|---|---|---|
| 4,155,870 | 5/1979 | Jorgensen | 252/131 |
| 4,278,657 | 7/1981 | Tezuka et al. | 424/63 |
| 4,400,295 | 8/1983 | Ootsu et al. | 252/356 |
| 4,495,070 | 1/1985 | Good | 252/106 |
| 4,543,205 | 9/1985 | Contamin | 252/546 |
| 4,673,525 | 6/1987 | Small et al. | 252/132 |
| 4,708,813 | 11/1987 | Snyder | 252/90 |
| 4,774,016 | 9/1988 | Gazanni | 252/170 |

*Primary Examiner*—Paul Lieberman
*Assistant Examiner*—Kevin McCarthy
*Attorney, Agent, or Firm*—Gordon W. Hueschen

[57] ABSTRACT

A clear, transparent, well-balanced gel facial cleanser formulation having a neutral pH, which is non-foaming and characterized by rapid rinseability, consisting essentially of the following ingredients: mild nonionic detergent and wound cleanser, moisturizer/humectant, moisturizer/emollient, gelling agent, viscosity stabilizer, pH adjuster, substantive emollient, preservative or bacterial inhibitor, solubilizer, and masking agent, the remainder being water, and the ratio of moisturizers excluding water to detergent being at least 2 to 1, is disclosed.

4 Claims, No Drawings

CLEAR NEUTRAL NON-FOAMING RAPIDLY-RINSABLE GEL FACIAL CLEANSER FORMULATION

BACKGROUND OF THE INVENTION

1. Field of Invention

Facial cleanser formulations.

2. Prior Art

Innumerable facial cleansers have been proposed in the prior art. Most of these have an alkaline pH, many are foaming, and most all suffer from excessive harshness and inability to be rinsed away rapidly. Moreover, in addition to comprising harsh surfactants, the ratio of surfactant to moisturizer is usually excessively high, when a moisturizer is present, and most must be excessively perfumed to cover harsh or unpleasant base notes.

The present invention provides a clear, transparent gel facial cleanser which comprises a mild nonionic detergent and which is suitable for employment even with sensitive skin, the detergent employed also doubling as a mild skin wound cleansing agent, which does not require excessive perfumery, which is nonfoaming and which is characterized by rapid rinseability, which contains a substantive moisturizer (which sticks to the skin) and provides a better balance with more emollient and less stripping and drying of the skin resulting from application of the gel facial cleanser of the present invention. The gel facial cleanser of the invention is moreover characterized by a ratio of moisturizers to detergent or surfactant of at least 2 to 1, and a neutral non-alkaline pH. It thus is suitable for daily cleansing and can illustratively be applied from pre-wetted hands with gently massage and rinsed away rapidly with cool water, whereafter the face may illustratively be dried by patting or the like. Moreover, it is especially suitable for the removal of makeup, in which case it may illustratively be applied directly to cotton balls, the makeup area gently massaged with re-application of fresh cotton balls if necessary, rinsing with warm water followed by cool water, and drying by patting or the like. The product is an attractive clear gel, is mild enough even for the most sensitive skin, includes a unique mild detergent and skin wound cleansing agent and, with a neutral, non-alkaline pH and a substantive moisturizer, and an at least 2 to 1 moisturizer to surfactant ratio, being non-foaming and characterized by rapid rinseability, is a superior all-purpose facial cleanser formulation which is at one and the same time cosmetically attractive and mild but nevertheless extremely effective.

OBJECTS OF THE INVENTION

It is an object of the present invention to provide a new and improved facial cleanser formulation. A further object is to provide a novel gel facial cleanser formulation characterized by better balance, as aforesaid, and which is cosmetically attractive and extremely efficient although of sufficient mildness so that it is suitable for use on sensitive skins. Another object of the invention is to provide a clear gel facial cleanser formulation containing a mild nonionic detergent which doubles as a wound-cleansing agent and having the characteristics and advantages set forth in the foregoing and which does not require excessive perfumery to cover harsh or unpleasant base notes. Further objects of the present invention will become apparent hereinafter and still others will be apparent to one skilled in the art to which this invention pertains.

SUMMARY OF THE INVENTION

My invention, then, comprises the following, inter alia:

A clear, transparent well-balanced gel facial cleanser formulation having a neutral pH, which is non-foaming and characterized by rapid rinseability, consisting essentially of the following ingredients:

(2) mild nonionic detergent and wound cleanser about 2% to 18%, (3) moisturizer/humectant about 5% to 15%, (4) moisturizer/emollient about 5% to 10%, (5) gelling agent about 1% to 10%, (6) viscosity stabilizer about 0.2% to 2%, (7) pH adjuster about 0.2% to 2%, (8) substantive emollient about 0.1% to 2%, (9) preservative or bacterial inhibitor about 0.05% to 0.2%, (10) solubilizer about 0.01% to 0.1%, and (11) masking agent about 0.01% to 0.1%, the remainder being (1) deionized or distilled water to 100%, all percentages being by weight and the ratio of combined (3), (4), and (8) to (2) being at least 2 to 1;

such a formulation wherein the detergent and wound cleanser is Poloxamer 188, wherein the moisturizer/humectant is a polyethylene glycol which is a clear viscous liquid at room temperature, wherein the moisturizer/emollient is PPG-10 methyl glucose ether, wherein the gelling agent comprises an acrylic copolymer, wherein the viscosity stabilizer is lauryl pyrrolidone, wherein the pH adjuster is triethanolamine, wherein the substantive emollient is quaternium-22, wherein the bacterial inhibitor is quaternium-15, wherein the solubilizer is PEG-40 castor oil, and wherein the masking agent is an essential oil; and such a formulation wherein the poloxamer 188 is present in an amount of about 5%, the polyethylene glycol is PEG-8 present in an amount of about 5%, the PPG-10 methyl glucose ether is present in an amount of about 5%, the acrylic copolymer is present in an amount of about 2.5%, the lauryl pyrrolidone is present in an amount of about 0.5%, the triethanolamine is present in an amount of about 0.5%, the quaternium-22 is present in an amount of about 0.1%, the quaternium-15 is present in an amount of about 0.05%, the PEG-40 castor oil is present in an amount of about 0.015%, and the essential oil is present in an amount of about 0.015%.

SPECIFIC DESCRIPTION OF THE INVENTION

The following Examples are given to illustrate the present invention, but are not to be construed as limiting:

EXAMPLE 1

GEL FACIAL CLEANSER

| Raw Materials | % By Weight | 1000 gram Batch | Procedure |
| --- | --- | --- | --- |
| Deionized Water | 75.73 | 757.3 | Using 1500 cc tared Beaker and shaft with propeller. Heat to 60° C. and remove from heat. |

| Raw Materials | % By Weight | 1000 gram Batch | Procedure |
|---|---|---|---|
| Pluronic F-68 | 5.0 | 50.0 | Add slowly to above while mixing. |
| Polyethylene Glycol 400 | 5.0 | 50.0 | Mix and add to above; rinse beaker with portion of batch. |
| Glucam P-10 | 5.0 | 50.0 | |
| Acrysol ICS-1 | 2.6 (2.5 cc) | 26.0 (25 cc) | Add slowly to above while mixing. |
| 50% w/w Triethanolamine (99%) | 0.64 (0.6 cc) | 6.4 (6 cc) | Add slowly to above while mixing. |
| Surfadone LP-300 | 0.45 (0.5 cc) | 4.5 (5 cc) | Add slowly to above while mixing. |
| Deionized Water | 5.0 | 50.0 | Mix and add to above; rinse beaker with portion of batch. |
| Ceraphyl 60 | 0.1 | 1.0 | |
| 50% w/w Triethanolamine (99%) | 0.4 | 4.0 | |
| Dowicil 200 | 0.05 | 0.5 | Add to above while mixing. |
| Surfactol 365 | 0.015 | 0.15 | Pre-mix before adding to above. Mix for ten minutes. |
| Oil #32578 (Natural Lavender oil masking agent) | 0.015 | 0.15 | |
| | 100.00 | | |

Check for water loss and add back any water lost; mix for fifteen minutes. Because of aeration caused by mixer, batch (closed container) is maintained in 40° C. oven to remove air, poured into appropriate containers, and cooled.

| Specifications: | |
|---|---|
| Color | Clear, colorless |
| Appearance | Soft gel |
| Odor | per standard, mild lavender |
| pH | 7.0-7.1 |
| Brookfield | (No. 4 spindle @ 12 RPM) 70-90 |
| Specific Gravity | 1.02 |

The gel facial cleanser formulation of Example 1 of the present invention is subjected to clinical evaluation and found to be extremely satisfactory and well balanced, even when applied to sensitive skin. It has the advantage of non-foamability but ready rinseability, and the emollients present therein leave the skin with a clean but pleasant skin feel without stripping and/or drying of the skin, while minor imperfections, cracks, or blemishes are effectively cleaned with the mild nonionic detergent and wound cleanser (Pluronic F-68) present therein.

EXAMPLE 2

GEL FACIAL CLEANSER

The procedure of Example 1 is repeated, using the following ingredients in amounts over the ranges stated, the total amount being brought to 100% by weight by the addition of deionized or distilled water. Within the ranges stated in the third column, those found to be optimum are those amounts stated in approximate figures in Column 2.

| TRADE/ CHEMICAL NAME | PERCENT BY WGT. | RANGE % BY WEIGHT |
|---|---|---|
| (1) Water | qs 100 | |
| (2) Pluronic F-68 | 5 | 2-18 |
| (3) Polyethylene Glycol 400 | 5 | 5-15 |
| (4) Glucam P-10 | 5 | 5-10 |
| (5) Acrysol ICS 1 | 2.5 | 1-10 |
| (6) Surfadone LP-300 | .5 | .2-2 |
| (7) Triethanolamine, 99% | .5 | .2-2 |
| (8) Ceraphyl 60 | .1 | .1-2 |
| (9) Dowicil 200 | .05 | .05-.2 |
| (10) Surfactol 365 | .015 | .01-.1 |
| (11) Essential Oil Masking Agent (#32578 or the like) | .015 | .01-.1 |

The product is subjected to clinical evaluation and found to be equally acceptable as the product of Example 1.

EXAMPLE 3

GEL FACIAL CLEANSER

A further production run of the gel facial cleanser formulation of the present invention is carried out in accord with the procedure of Example 1, using the ingredients and the approximate amounts set forth in the following, the total amount being brought to the required 100% by weight by the addition of deionized or distilled water.

| TRADE/ CHEMICAL NAME | PERCENT BY WGT. | CTFA NAME |
|---|---|---|
| (1) Water | qs 100 | Deionized or Distilled Water |
| (2) Pluronic F-68 | 5 | Poloxamer 188 |
| (3) Polyethylene Glycol 400 | 5 | PEG-8 |
| (4) Glucam P-10 | 5 | PPG-10 Methyl Glucose Ether |
| (5) Acrysol ICS-1 | 2.5 | Acrylates, Steareth-20, Methacrylate Copolymer |
| (6) Surfadone LP-300 | .5 | Lauryl Pyrrolidone |
| (7) Triethanolamine, 99% | .5 | Triethanolamine |
| (8) Ceraphyl 60 | .1 | Quaternium-22 |
| (9) Dowicil 200 | .05 | Quaternium-15 |
| (10) Surfactol 365 | .015 | PEG-40 Castor Oil |
| (11) Essential Oil (#32578) | .015 | Essential Oil |

The product is subjected to clinical evaluation in the same manner as the product of Example 1 and is found to be equally satisfactory as the product of Example 1.

The essential ingredients of the gel facial cleanser formulation of the present invention are as set forth in the following, with their more specific identification set forth in the second column. In the third column is set forth the range of percentage by weight of the essential ingredients of the gel facial cleanser formulation of the present invention and, in the fourth column, the preferred percentage by weight.

TABLE I

| INGREDIENTS: | DEFINITION OR CHARACTERIZATION | RANGES, % BY WEIGHT | PREFERRED % BY WEIGHT |
|---|---|---|---|
| (1) Water | Moisturizer/Co-solvent | to 100% | |
| (2) Poloxamer 188 | Mild Wound Cleanser | 2-18 | ca 5 |
| (3) PEG-8 | Moisturizer/Humectant | 5-15 | ca 5 |
| (4) PPG-10 Methyl Glucose Ether | Moisturizer/Emollient | 5-10 | ca 5 |
| (5) Acrylates, Steareth-20 Methacrylate Copolymer | Gelling Agent | 1-10 | ca 2.5 |
| (6) Lauryl Pyrrolidone | Viscosity Stabilizer | .2-2 | ca .5 |
| (7) Triethanolamine | pH Adjuster | .2-2 | ca .5 |
| (8) Quaternium-22 | Substantive Emollient | .1-2 | ca .1 |
| (9) Quaternium-15 | Preservative or Bacterial Inhibitor | .05-.2 | ca .05 |
| (10) PEG-40 Castor Oil | Solubilizer for Masking Agent | .01-.1 | ca .015 |
| (11) Essential Oil | Masking Agent | .01-.1 | ca .015 |

The suppliers of the active ingredients of the compositions of the invention along with the tradenames for the ingredients and the CTFA (Cosmetic, Toiletry, and Fragrance Association) names for the ingredients are set forth in the following tabulation, it being understood that substitution of other functionally equivalent moisturizers, co-solvents, mild wound cleansers, moisturizer/humectants, moisturizer/emollients, clear gelling agents, viscosity stabilizers, pH adjusters, substantive emollients, bacterial inhibitors, solubilizers, and masking agents may be made wherever necessary or desirable, so long as the excellent and desirable characteristics of the gel facial cleanser formulation of the present invention are not essentially changed by the substitution.

TABLE II

| Supplier | Trade Name | CTFA Name |
|---|---|---|
| BASF Corporation | (2) Pluronic F-68 (Polyoxypropylene-polyoxyethylene Block Copolymer) | Poloxamer 188 |
| Union Carbide | (3) Polyethylene Glycol 400 (polymers of ethylene oxide which can be represented by the general formula HO (CH$_2$CH$_2$O)$_n$H, where n represents the average number of ethylene oxide units) | PEG-8 |
| Amerchol | (4) Glucam P-10 [(Propoxylated (10 moles) methyl glucoside)] | PPG-10 Methyl Glucose Ether |
| Rohm & Haas | (5) Acrysol ICS-1 (Acrylic Copolymer - 30% solids - some residual monomer) | Acrylates, Steareth-20, Methacrylate Copolymer |
| GAF Corporation | (6) Surfadone LP-300 (N-Dodecyl-2-Pyrrolidone) | Lauryl Pyrrolidone |
| | (7) Triethanolamine | Triethanolamine |
| VanDyk | (8) Ceraphyl 60 (Gluconamidopropyl dimethyl-2-hydroxyethyl ammonium chloride) | Quaternium-22 |
| Dow Chemical | (9) Dowicil 200 (Cis isomer of 1-(3-chloroallyl)-3,5,7-triaza-1-azoniaadamantane chloride | Quaternium-15 |
| Cas Chem | (10) Surfactol 365 (nonionic surfactant) | PEG-40 Castor Oil |
| Carrubba | (11) Oil #32578 (Natural Lavender Oil) | Natural Oil |

Reference is made to U.S. Pat. No. 4,673,525, the disclosure of which is incorporated herein by reference for moisturizer/emollients which may be substituted in the composition of the present invention as well as for other nonionic surfactants, polymers or otherwise, which may be substituted for the mild nonionic surfactant and wound cleanser Poloxamer 188 as used in the foregoing, as well as other optional ingredients which may or may not be included in the composition of the present invention depending upon the objectives of the formulator. Moreover, in place of the moisturizer/humectant employed according to the present invention, also polypropylene glycol, other polyglycols, glycerine, and sorbital may be employed as well as other moisturizer/humectants based upon these fundamental units. The polyethylene glycols are clear, viscous. liquids at room temperature and Polyglycols 200, 300, 400, or 600 may be employed, although Polyglycol 400 is definitely preferred.

In place of the gelling agent or thickener of the present invention, which clears up to a clear gel upon neutralization and gelation, other acrylic copolymers may be employed or other thickeners or gelling agents so long as they fulfill the requirement of clearing up upon neutralization and gelation. Moreover, as additional viscosity stabilizers which may be employed instead of or in addition to the lauryl pyrrolidone may be mentioned methocel and other cellulose derivatives, to name a few. In place of the pH adjuster of the present invention, triethanolamine, as neutralizers other tertiary amines and the like may be employed with equal facility. As a substantive emollient instead of the Quaternium-22 may be employed the polymer JR 400, a cationic cellulosic ether which is a water-soluble sodium salt available from Union Carbide and which has the CAS name as follows: Cellulose, ω-ether with α-[2-hydroxy-3-(trimethylammonio)propyl]-ω-hydroxy poly(oxy-1,2-ethanediyl)chloride.

In place of the bacterial inhibitor or preservative Quaternium-15, methyl and propyl parahydroxybenzoates may be illustratively employed. In place of the solubilizer for the masking agent, which according to the foregoing is the PEG-40 castor oil, which is a nonionic surfactant used to solubilize the masking agent oil, alternatives may be employed such as Tween 20 which is polyoxyethylene 20 or polysorbate 20, which is sorbitan monolaurate. As far as the triethanolamine, it is provided in liquid aqueous form and, as employed in the examples hereof was of a 99% concentration, although other aqueous forms of triethanolamine are available having lower concentrations, and such triethanolamine aqueous solutions, as well as other tertiary amine and similar neutralizers, may be employed in place of the triethanolamine with equal facility.

It is accordingly seen from the foregoing that the present invention provides a highly desirable and advantageous clear gel facial cleanser formulation which comprises an extremely well-balanced mild facial cleanser suitable even for sensitive skin and which is at the same time a unique mild skin wound cleansing agent, which is non-foaming and characterized by rapid rinseability, which is at a neutral non-alkaline pH and which contains a substantive moisturizer and at least a 2 to 1 moisturizer to detergent or surfactant ratio, which is efficient and yet sufficiently mild so that it can be used upon even the most sensitive skin and which, in its cleansing aspect, leaves the facial skin efficiently clean, but yet soft and with a pleasant and totally-acceptable skin "feel", the same being a clean, refreshed, and unusually smooth and moisturized "feel" without stripping and drying of the skin, especially when compared with usual prior art facial cleanser formulations.

It is to be understood that the present invention is not to be limited to the exact compounds, compositions, procedures, or formulations disclosed, as numerous modifications and changes therein will immediately become apparent to one skilled in the art to which this invention pertains, wherefore the present invention is to be understood as limited only by the full scope which can be legally accorded to the appended claims.

I claim:

1. A clear, transparent, well-balanced gel facial cleanser formulation having a neutral pH, which is non-foaming and characterized by rapid rinseability, consisting essentially of the following ingredients:
   (2) mild nonionic detergent and wound cleanser comprising a polyoxypropylene-polyoxyethylene block copolymer 2% to 18%, (3) moisturizer/humectant comprising a clear viscous liquid polyethylene glycol 5% to 15%, (4) moisturizer/emollient comprising a propoxylated methyl glucoside 5% to 10%, (5) gelling agent comprising an acrylic copolymer 1% to 10%, (6) viscosity stabilizer 0.2% to 2%, (7) pH adjuster 0.2% to 2%, (8) substantive emollient 0.1% to 2%, (9) preservative or bacterial inhibitor, the remainder being (1) deionized or distilled water to 100%, all percentages being by weight, and the ratio of (3), (4), and (8) combined to (2) being at least 2 to 1.

2. The formulation of claim 1 wherein the detergent and would cleanser comprises poloxamer 188, wherein the moisturizer/humectant comprises a polyethylene glycol which is a clear viscous liquid at room temperature, wherein the moisturizer/emollient comprises PPG-10 methyl glucose ether, wherein the gelling agent comprises an acrylic copolymer, wherein the viscosity stabilizer comprises lauryl; pyrrolidone, wherein the pH adjuster is triethanolamine, wherein the substantive emollient comprises quaternium-22, and wherein the bacterial inhibitor comprises quaternium-15.

3. A clear, transparent, well-balanced gel facial cleanser formulation having a neutral pH, which is non-foaming and characterized by rapid rinseability, consisting essentially of the following ingredients:
   (2) mild nonionic detergent and wound cleanser comprising poloxamer 1882% to 18%, (3) moisturizer/humectant comprising a polyethylene glycol which is a clear viscous liquid at room temperature 5% to 15%, (4) moisturizer/emollient comprising PPG-10methyl glucose ether 5% to 10%, (5) gelling agent comprising an acrylic copolymer 1% to 10%, (6) viscosity stabilizer comprising lauryl pyrrolidone 0.2% to 2%, (7) pH adjuster comprising a tertiary amine 0.2% to 2%, (8) substantive emollient comprising quaternium 22 0.1% to 2%, (9) preservative or bacterial inhibitor 0.05% to 0.2%, (10) solubilizer comprising PEG castor oil 0.01% to 0.1%, and (11) masking agent comprising an essential oil 0.1% to 0.1%, the remainder being (1) deionized or distilled water to 100%, all percentages being by weight, and the ratio of (3), (4), and (8) combined to (2) being at least 2 to 1.

4. The formulation of claim 3 wherein the poloxamer 188 is present in an amount of about 5%, the polyethylene glycol comprises PEG-10 methyl glucose ether is present in an amount of about 5%, the acrylic copolymer is present in an amount of about 2.5%, the lauryl pyrrolidone is present in an amount of about 0.5%, the tertiary amine comprises triethanolamine present in an amount about 0.5%, the quaternium-22 is present in an amount of about 0.1%, the preservative comprises quaternium-15 present in an amount of about 0.05%, the PEG-40 castor oil is present in an amount of about 0.015%, and the essential iol is present in an amount of about 0.015%.

* * * * *

UNITED STATES PATENT AND TRADEMARK OFFICE
CERTIFICATE OF CORRECTION

PATENT NO. : 5,030,374
DATED : July 9, 1991
INVENTOR(S) : Frank Tranner It is certified that error appears in the above-identified patent and that said Letters Patent is hereby corrected as shown below:

Title Page, [56] References Cited, U.S. PATENT DOCUMENTS, line 4;
 "4,495,070" should read -- 4,495,079 --
Title Page, [56] References Cited, U.S. PATENT DOCUMENTS, line 8 (last line);
 "Gazanni" should read -- Gazzani --
Col. 5, approximately lines 48 & 49; "[(Propoxylated (10 moles) methyl
 glucoside)]" should read -- (Propoxylated (10 moles) methyl glucoside) --
Col. 8, line 8; "lauryl;" should read -- lauryl --

Col. 8, line 18; "1882%" should read -- 188 2% --

Col. 8, line 22; "-10methyl" should read -- -10 methyl --

Col. 8, line 31; "0.1%" (first occurrence) should read -- .01% --

Col. 8, line 37; after "PEG-" insert -- 8 present in an amount of about 5%, the PPG-"
Col. 8, line 46; "iol" should read -- oil --

Col. 6, line 30; "employed" should read -- employed, --

Signed and Sealed this

Thirteenth Day of October, 1992

*Attest:*

DOUGLAS B. COMER

*Attesting Officer*  *Acting Commissioner of Patents and Trademarks*